United States Patent
Aldrich

(10) Patent No.: US 6,397,093 B1
(45) Date of Patent: May 28, 2002

(54) NON-INVASIVE CARBOXYHEMOGLOBIN ANALYZER

(75) Inventor: Thomas K. Aldrich, Pelham, NY (US)

(73) Assignee: Essential Medical Devices, Inc., Pelham, NY (US)

( * ) Notice: Subject to any disclaimer, the term of this patent is extended or adjusted under 35 U.S.C. 154(b) by 0 days.

(21) Appl. No.: 09/514,791

(22) Filed: Feb. 28, 2000

Related U.S. Application Data

(63) Continuation-in-part of application No. 09/158,030, filed on Sep. 22, 1998, now abandoned, which is a continuation-in-part of application No. 08/759,582, filed on Dec. 5, 1996, now Pat. No. 5,810,723.

(51) Int. Cl.⁷ .................................................. A61B 5/00
(52) U.S. Cl. ........................................ 600/330; 600/323
(58) Field of Search ................................. 600/310, 322, 600/323, 330, 336

(56) References Cited

U.S. PATENT DOCUMENTS 5,413,100 A * 5/1995 Barthelemy et al. ........ 600/326
5,638,816 A * 6/1997 Kiani-Azarbayjany et al. .. 600/316

* cited by examiner

Primary Examiner—Eric F. Winakur
(74) Attorney, Agent, or Firm—Patterson, Belknap, Webb & Tyler, LLP

(57) ABSTRACT

An apparatus and method is disclosed which allows the non-invasive monitoring of a subject's carboxyhemoglobin level, thereby allowing the detection of possible carbon monoxide poisoning. The subject breathes oxygen to saturate his blood hemoglobin and eliminate reduced hemoglobin, thus allowing the detection and differentiation between oxy- and carboxyhemoglobin by modification of a conventional pulse oximeter. Preferably the device works in two modes. The first mode is a conventional pulse oximeter capable of determining the level of oxy-hemoglobin in the subject's arterial blood. Upon the achievement of certain criteria the preferred embodiment of the inventive device would switch to a second mode, in which mode the device would be capable of determining carboxyhemoglobin levels. Alternatively, carboxyhemoglobin can be measured using two devices and two different pairs of wavelengths transilluminating two different body parts.

9 Claims, 8 Drawing Sheets

NON-INVASIVE CARBOXYHEMOGLOBIN ANALYZER

This application is a continuation-in-part of U.S. application Ser. No. 09/158,030, filed Sep. 22, 1998 now abandoned, which is in turn a continuation-in-part of U.S. application Ser. No. 08/759,582 filed Feb. 5, 1996, which issued as U.S. Pat. No. 5,810,723 on Sep. 22, 1998.

BACKGROUND OF THE INVENTION

1. Field of the Invention

The present invention is directed to a non-invasive device and method for detecting possible carbon monoxide poisoning by determining the percentage of carboxyhemoglobin (CO-Hgb) in the subject's blood. The non-invasive device for determining the percentage of carboxyhemoglobin in blood is a pulse oximeter modified to discriminate between oxy- and carboxyhemoglobin. Preferably the device works in two modes. The first mode is a conventional pulse oximeter capable of determining the level of oxyhemoglobin (hemoglobin saturated with oxygen) in the subject's arterial blood. Upon the achievement of certain criteria, described below, the preferred embodiment of the inventive device would switch to a second mode, in which mode the device would be capable of determining carboxyhemoglobin levels.

The device is used in a method for measuring carboxyhemoglobin which includes having the subject breathe oxygen to convert reduced hemoglobin to oxy-hemoglobin, thereby removing reduced hemoglobin as a blood constituent, determining the concentration of the principle two remaining hemoglobin constituents in the blood (oxy- and carboxy) and measuring carboxyhemoglobin by the modified pulse oximeter.

2. Description of the Prior Art

Carbon monoxide (CO) poisoning is an important cause of morbidity and mortality in the United States that often goes unsuspected and therefore is not promptly treated. Sadovnikoff N, Varon J, Sternbach G L, Carbon monoxide poisoning: an occult epidemic, *Postgraduate Medicine,* 92:86–96 (1992)(incorporated by reference); Kales S N, Carbon monoxide intoxication, *Am Fam Phys,* 48:1100–4 (1993)(incorporated by reference). CO intoxication is the leading cause of death by poisoning in the U.S. and accounts for approximately 3,800 accidental and suicidal deaths annually. Nonlethal CO poisoning occurs as well, but statistics are not available on the number of incidents of such occurrences. Occult CO poisoning is a type of subacute poisoning caused by an unrecognized source of CO in the home or other indoor environment. Many nonlethal exposures go undetected.

Smoke inhalation from fires accounts for the majority of CO exposure. Firefighters are at high risk. Other sources include furnaces, gas-powered engines, pool heaters and wood stoves.

CO combines preferentially with hemoglobin to produce carboxyhemoglobin, displacing oxygen and reducing systemic arterial oxygen content. CO binds reversibly to hemoglobin with an affinity more than 200 times that of oxygen. Inhaled CO rapidly diffuses across the alveolar-capillary membranes into the bloodstream, where the reversible binding with hemoglobin occurs and carboxyhemoglobin is formed. Carboxyhemoglobin decreases the amount of hemoglobin available for oxygen transport and also results in decreased release of oxygen to tissues.

Symptoms of acute CO poisoning are more dramatic than those of chronic exposure. Subacute or chronic CO poisoning may present less characteristic symptoms and patients may initially be misdiagnosed. The most common misdiagnosis is "flu-like" syndrome. At low carboxyhemoglobin levels in chronic CO poisoning, chronic cardiopulmonary problems may be exacerbated. Therefore, chest pains caused by reduced myocardial oxygen delivery due to CO poisoning may be misdiagnosed.

Acute exposure to CO correlates to various symptoms. At carboxyhemoglobin levels of above 10% the victim may be asymptomatic or have a headache. At 20%, CO exposure causes dizziness, confusion and nausea. Between 20 and 50% carboxyhemoglobin levels, the subject experiences visual disturbances, confusion and syncope. At levels above 50% the subject experiences seizures and coma, and death is likely at levels of carboxyhemoglobin above 60%. Sublethal acute exposure leaves some victims with permanent neurologic sequelae.

When CO poisoning is suspected, the diagnosis is usually established either by detection of abnormally high CO in expired air or by analysis of arterial or venous blood for carboxyhemoglobin. Both of these techniques require instrumentation that is not readily available to paramedics or emergency rooms. In addition, because of the lapse of time between the exposure and the test, confirming the diagnosis may be difficult in some patients. Carboxyhemoglobin levels as tested by the lab may be low or undetectable because of the time elapsed between the exposure and taking of the sample.

The analysis of arterial and venous blood samples requires taking a blood sample by arterial or veni puncture or by finger prick, which raises small, but important concerns regarding pain and the potential for transmission of infectious disease, such as vial hepatitis and human immunodeficiency virus (HIV) infection. In addition, analysis of the arterial or venous blood sample is usually done by spectrophotometric means, as disclosed in U.S. Pat. Nos. 4,997,769 and 5,491,341. Such analytic methods require bulky instrumentation.

Tests done after the exposure must be treated with caution. While elevated carboxyhemoglobin levels found by testing blood samples will confirm the diagnosis of CO intoxication, low and moderately increased values must be interpreted with caution. The half-life of carboxyhemoglobin is about four hours when breathing room air and about one hour when breathing pure oxygen. Thus, the carboxyhemoglobin level obtained upon taking the blood sample must be used to extrapolate to the patient's peak level.

The recent marketing of inexpensive home ambient air CO monitors has increased the frequency with which CO poisoning is reported, many times inaccurately. The increase of such reports requires an increase in EMS visits to investigate. For example, during two cold spells in 1994, the Chicago Fire Department logged over 50,000 calls for suspected CO poisoning, most of which were not corroborated, and many of which resulted in Emergency Room visits to exclude CO intoxication.

The subject must be removed from the source of CO if exposure is suspected. Supplemental oxygen, ventilatory support and monitoring for cardiac arrhythmias are the mainstays of therapy for CO poisoning. Administration of 100% oxygen is usually done as soon as CO poisoning is suspected and before laboratory confirmation is obtained. Since many hospitals send blood samples to distant labs for analysis of carboxyhemoglobin levels, the treating physician must initiate treatment empirically.

Transportation to an appropriate center for hyperbaric oxygen therapy is a method of treatment in severe cases.

Hyperbaric oxygen at a pressure of 3 atmospheres reduces the elimination half-life of carboxyhemoglobin to less than 30 minutes and can dissolve enough oxygen to sustain life even in the absence of hemoglobin. In such severe cases of CO poisoning, time is of the essence. There are a limited number of hyperbaric oxygen centers available. The location of a suitable center and transportation of the subject can take some time. Therefore, waiting for lab analysis can be a severe limitation on the treatment of such a subject.

Typical lab analyses include analysis by CO-oximeters and/or gas chromatography. However, as stated above, the drawbacks of relying on these methods are the need to draw arterial blood and the prolonged delay between sample acquisition and the availability of the laboratory results. CO-oximeters are laboratory instruments that measure oxy-, reduced-, carboxy-, and met-hemoglobins (and sometimes also sulf-hemoglobin) in blood samples by analyzing absorbance at multiple wavelengths, chosen to optimally separate the various types of hemoglobin. Mahoney J J, Vreman H J, Stevenson D K, Van Kessel A L. Measurement of carboxyhemoglobin and total hemoglobin by five specialized spectrophotometers (CO-oximeters) in comparison with reference methods, *Clinical Chemistry,* 39:1693–1700 (1993) (incorporated by reference); Steinke J M, Shepherd A P, Effects of temperature on optical absorbance spectra of oxy-, carboxy-, and deoxyhemoglobin, *Clinical Chemistry,* 38:1360–4 (1992)(incorporated by reference); Zijlstra W G, Buursma A, Zwart A, Performance of an automated six-wavelength photometer (Radiometer OSM3) for routine measurement of hemoglobin derivatives, *Clinical Chemistry,* 34:149–52 (1988)(incorporated by reference). CO-oximeters are commercially available from manufacturers such as Radiometer Als, Instrumentation Laboratories and Ciba-Coming.

CO-oximetry is not a non-invasive method of measuring blood constituents, inasmuch as it requires removal of an arterial blood sample. Although there are potential errors in CO-oximetry measurements, produced by the presence of abnormal hemoglobins or dyes, changes in oxygenation of the sample after withdrawal but before measurement, and other factors, CO-oximetry represents a reasonable method to obtain accurate measurements of carboxyhemoglobin levels, albeit time consuming.

A better standard for measuring carboxyhemoglobin can be provided by gas-chromatographic measurements of the carbon monoxide evolved from hemolyzed blood samples treated with $K_3Fe(CN)_6$ to convert all hemoglobin to met-hemoglobin. Fogh-Andersen N, Eriksen P S, Grimsted J, Siggaard-Andersen O, Gas-chromatographic measurement of carboxyhemoglobin in blood from mothers and newborns, *Clin Chem,* 34:24–6 (1988)(incorporated by reference). However, gas chromatography is generally limited to research laboratories because it is complex and time consuming and requires specialized skills for proper operation.

Pulse oximeters are non-invasive monitors of arterial blood oxygen saturation. They are used to determine the fraction of oxyhemoglobin in arterial blood. The technology was developed in the 1970's and 80's, and has become indispensable in emergency rooms, operating rooms, and intensive care units. The instruments take advantage of the differing light absorbance spectra of oxy- and reduced hemoglobin to measure the fractional concentration of oxyhemoglobin present in arterial blood. Mendelson Y, Pulse oximetry: theory and applications for noninvasive monitoring, *Clinical Chemistry,* 38:1601–7 (1992) (incorporated by reference); Hanning C D, Alexander-Williams J M, Pulse oximetry: a practical review, *BMJ* 311:367–70 (1995)(incorporated by reference); Lindberg L G, Lennmarken C, Vegfors M, Pulse oximetry—clinical implications and recent technical developments, *Acta Anaesthesiol Scand,* 39: 279–87 (1995)(incorporated by reference).

Pulse oximeters compute oxygen saturation (the relative amount of oxygen carried by the hemoglobin in arterial blood) by measuring differences in the visible and near infrared absorbances of fully oxygenated and deoxygenated arterial blood. Unlike clinical blood gas analyzers, which require a sample of blood from the patient and can provide only intermittent measurement of patient oxygenation, pulse oximeters provide continuous, safe and instantaneous measurement of blood oxygenation.

In conventional pulse oximeters, light produced by two light-emitting diodes (LED's) at approximately 660 nm (red) and 940 nm (infrared) are alternately passed through the subject's finger, toe, or ear (or other well-perfused tissue), and the transmitted light is measured by a rapidly-responding photodetector. At each of the two wavelengths, the resulting time-varying measurement of light intensity is roughly proportional to finger volume, which varies with the arterial pulse—a process termed "photoplethysmography". The light which is not transmitted to the photodetector is absorbed by the finger. The amount of absorbance depends on tissue density and the amount and character of the blood (venous and arterial) that is present in the light path.

Changes in absorbance (A) are caused by changes in the amount of blood present in the light path, assumed to be primarily change in the amount of arterial blood due to the arterial pulse. Because absorbance of oxy-hemoglobin differs for light at the two wavelengths, a ratio of change in absorbance of red to change in absorbance of infrared light can be used to measure oxy-hemoglobin percentage. In practice, transmittance ($T=10^{-A}$) is measured from each of the photoplethysmograms, which is mathematically corrected to yield absorbance. The two measurements are then electronically divided, and after inconsistent data points are discarded, the ratios are averaged to yield an average ratio of red/infrared absorbance change. The average ratio is then multiplied by a correction factor that has been empirically determined for each instrument by comparison with arterial blood samples measured with a CO-oximeter in normal subjects made hypoxemic, or in oxygen deficiency, caused by breathing gases of low fractions of inspired oxygen ($FiO_2$).

Commercial pulse oximeters used to measure the amount of arterial blood oxygen saturation ($SaO_2$) are available from the following manufacturers: BCI International, Biochem International, Inc., Criticare Systems, Inc., Datascope Corp., Datex Instrumentation Corp., Gambro Engstrom A. B., Invivo Research, Inc., Kontron Instruments, Life Care International, Inc., MSA, Medical Research Laboratories, Minolta Camera Co., Ltd., Nellcor-Puritan-Bennett, Nippon Colin Co., Ltd., Nonin Medical Systems, Inc., Ohmeda, Inc., Palco Labs. PhysioControl, Respironics, Inc., Sensor Medics Corp., Siemens Medical Systems, Inc., Simed Corp. and Spectramed, Inc.

Pulse oximeters can be controlled with various software packages, including those made by EMG Scientific. Signal processing apparatus, such as that disclosed in U.S. Pat. No. 5,490,505, can be used to process the signals generated by a pulse oximeter.

Prior designs of pulse oximeters used to measure arterial oxygen saturation are well known. For example, U.S. Pat.

No. 4,653,498 to New, Jr. et al. (1987) describes a display monitor for use with a pulse oximeter of the type wherein light of two different wavelengths is passed through body tissue, such as a finger, an ear or the scalp, so as to be modulated by the pulsatile component of arterial blood therein and thereby indicates oxygen saturation. Similarly, U.S. Pat. Nos. 4,621,643 (1986), 4,700,708 (1987) and 4,770,179 (1988), also to New, Jr. et al., describe disposable probes for use with pulse oximeters.

One problem with pulse oximeters is that they tend to measure carboxyhemoglobin as oxy-hemoglobin. At 940 nm, oxy-hemoglobin is the predominate absorber of light, while at 660 nm reduced hemoglobin is the main absorber. Carboxyhemoglobin also absorbs strongly at 660 nm. Vegfors M, Lennmarken C, Carboxyhaemoglobinaemia and pulse oximetry, *Brit J Anaesth*, 66:625–6 (1991) (incorporated by reference). Thus, a reading of 100% $SaO_2$ actually only indicates that no reduced hemoglobin is present; there may be any mixture of oxy- and carboxyhemoglobin. This eliminates pulse oximeters, as they are now manufactured, from being used as efficient instruments to detect elevated carboxyhemoglobin levels or to accurately detect the abnormally low level of oxyhemoglobin present in the blood of a patient with CO poisoning.

Adaptation of a pulse oximeter to measure carboxyhemoglobin as well as oxy- and reduced hemoglobins may be attempted by the use of three LED's at appropriate wavelengths, perhaps 579 nm (isobestic for reduced and carboxyhemoglobins), 649 nm (isobestic for oxy- and carboxyhemoglobins), and 803 nm (isobestic for oxy- and reduced hemoglobins), to allow separation of the three hemoglobins. In that case, somewhat more complex calculations than a simple ratio of changing absorbances would have to be made by the instrument to solve three simultaneous equations with three unknowns.

Devices which use this more complex method of additional LEDs are disclosed in U.S. Pat. Nos. 4,167,331, 5,355,880 and 5,412,100. Each of these devices is complex and hindered from practical use because of the need for a third wavelength.

Other attempts have been made to measure blood constituents. For example, U.S. Pat. No. 4,407,290 (1983) to Wilber, discloses a blood constituent concentration measuring device that is capable of measuring changes in blood thickness of such constituents relative to total thickness change of blood at a test area.

Additionally, Braig et al. in U.S. Pat. No. 5,313,941 discloses a method and apparatus for measuring blood constituents by monitoring infrared absorption of the desired blood constituent in the long infrared wavelength range, between 2–20 µm, preferably 9.1 µm for glucose. As Braig et al. recognizes, however, the use of long wavelength infrared energy may burn or cause patient discomfort. Therefore, the Braig et al. device requires that pulses of infrared energy (two or more) are sent per heart beat. In addition to the danger to the patient, this requires a more complex mechanical device.

Complex mathematical programs for calculating blood constituent levels from multiple variants are disclosed in U.S. Pat. Nos. 5,285,782 and 5,435,309. Both of these patents contemplate complete, multi-variant readings from their devices and the requisite microprocessor power to calculate the necessary algorithms.

Tehrani U.S. Pat. No. 4,909,259 teaches the determination of a subject's metabolic rate through the combined use of a $CO_2$ analyzer and an $O_2$ analyzer or a pulse oximeter to compare ratios of oxygen to carbon dioxide in the blood. Tehrani does not, however, disclose a non-invasive method for detecting carboxyhemoglobin levels in the blood.

For practical clinical purposes, met-hemoglobin and sulfhemoglobin can be ignored in most cases. However, various mixtures of oxy-, carboxy-, and reduced hemoglobin are commonly present in smokers, fire fighters, victims of fires, tunnel workers, persons using indoor kerosene heaters or wood-burning stoves, and persons who attempt suicide by exposure to natural gas or automobile exhaust. Thus, the development of a non-invasive monitor that can separate oxy- and carboxy-hemoglobins would serve a useful purpose.

The availability of a simple, inexpensive, non-invasive monitoring device for carboxyhemoglobin would greatly simplify diagnosis, and would lead to more rapid diagnosis of CO intoxication and consequently reduced morbidity from the neurologic and cardiac sequelae. By allowing appropriate triage by paramedics, such an instrument might also lead to reduced need for emergency room visits to exclude CO intoxication in patients with suggestive symptoms.

A non-invasive carboxyhemoglobin monitor would likely find a substantial market among hospital emergency rooms, community emergency medical services, fire departments, gas companies, among others.

SUMMARY OF THE INVENTION

In accordance with the invention, the above and other objects are met by the present non-invasive monitoring device and method for analysis of blood constituents.

The present invention for analyzing and monitoring carbon monoxide levels in a patient and detecting possible carbon monoxide poisoning is a pulse oximeter which measures the changing absorbencies at two wavelengths, one of which is a wavelength at which carboxy and oxy-hemoglobins absorb light to a similar degree and the second wavelength one where carboxy and oxy-hemoglobins absorb light at a different degree, for example, at 660 nm and 940 nm, and calibrated against known carboxyhemoglobin standards. Prior to using this device on a patient, the patient breathes oxygen at a sufficient flow rate to eliminate reduced oxygen. By doing so, with the exception of very small amounts of met- and sulf-hemoglobins, the only hemoglobin components of the arterial blood are oxy- and carboxyhemoglobin, which can be distinguished at the proposed wavelengths.

Accordingly, it is an object of the present invention to provide a simple, inexpensive, non-invasive monitoring device for carboxyhemoglobin.

It is another object of this invention to provide a device and method for simplifying diagnosis of CO intoxication and consequently reduce morbidity from the neurologic and cardiae sequelae.

It is another object of the present invention to provide a device and method for diagnosing CO intoxication which allows use on-site by paramedics and other emergency personnel, thus reducing the need for emergency room visits to exclude CO intoxication with suggestive symptoms.

Yet another object of the present invention is to provide accurate carboxyhemoglobin measurements using only 2 LEDs.

Another object of the present invention is to provide a device capable of working in and switching between two modes, the first as a conventional pulse oximeter and the second mode capable of determining levels of carboxyhemoglobin.

BRIEF DESCRIPTION OF THE DRAWINGS

Preferred embodiments of the non-invasive carboxyhemoglobin and blood hemoglobin analyzers of the present invention are described in detail below with reference to the drawings wherein.

DETAILED DESCRIPTION OF THE PREFERRED EMBODIMENTS

Figure 1:
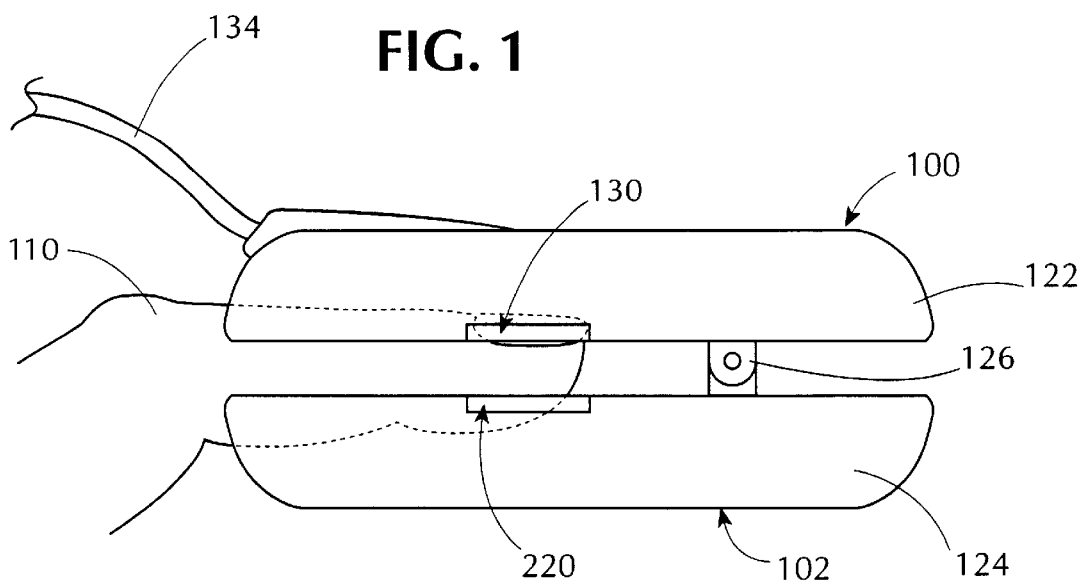
FIG. 1 is a drawing of the inventive device for measuring carboxyhemoglobin concentrations in a subject's blood.

As will become readily apparent to those skilled in the art, although the illustrations in the drawings and the description describe use of novel non-invasive carboxyhemoglobin analyzer, the various features described can be used alone or in combination with other features without departing from the scope of the invention set forth below in the claims.

The device described herein is a simple noninvasive instrument that measures carboxy and oxy-hemoglobin percentages when only those two species are present in amounts greater than 1–2%. The device in its preferred embodiment would be capable of working in two modes. The first mode is a conventional pulse oximeter used to measure saturated oxygen. Upon the achievement of certain conditions, described below, the device would be switchable to a second mode in which carboxyhemoglobin levels would be monitored.

The device illustrated in FIG. 1 is similar to currently-available pulse oximeters, with a modification that allows accurate carboxyhemoglobin measurements using only two LEDs.

The carboxyhemoglobin analyzer 100 is made up of clamp 102 with arms 122 and 124 which hold the patient's finger 110 in place. The clamp 102 can be modified to accept and hold a patient's toe or ear or other well-perfused tissue, as will be recognized by one skilled in the art. One of the arms 122 holds a set 130 of two LEDs, one of which emits light at a wavelength at which oxy- and carboxyhemoglobin absorb light approximately equally (one example being 660 nm (red)) and the other LED which emits light at a wavelength at which the absorbance of oxy- and carboxyhemoglobin differ markedly (one example being 940 nm (infrared)).

Figure 5:
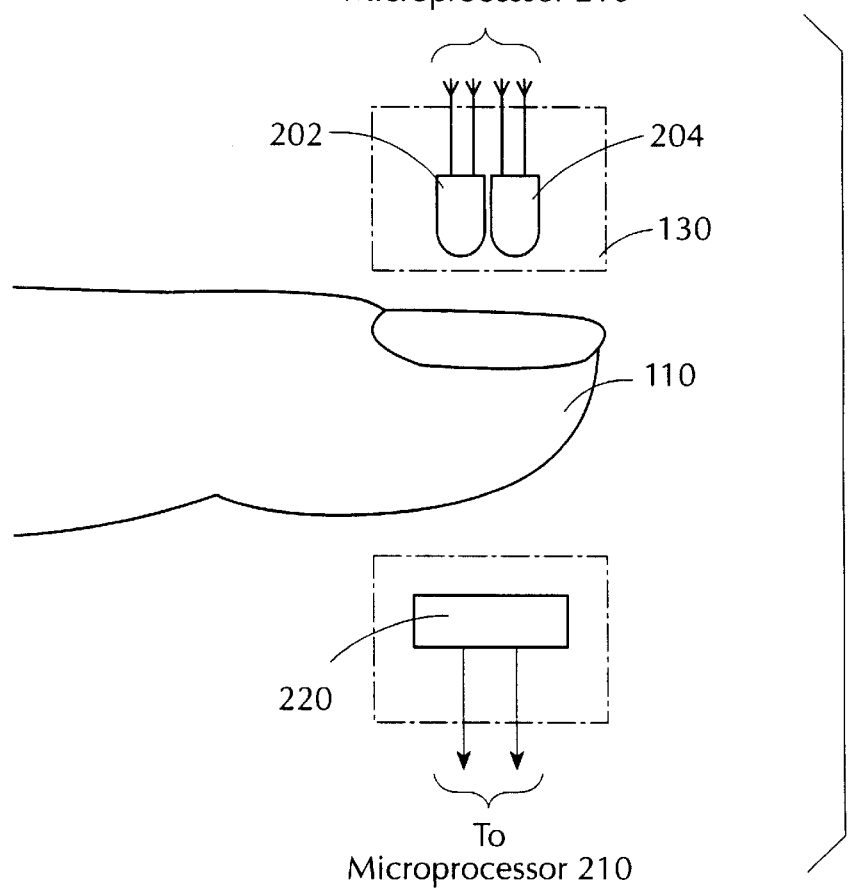
FIG. 5 is a detailed cutaway view of the inventive carboxyhemoglobin analyzer.
Figure 2:
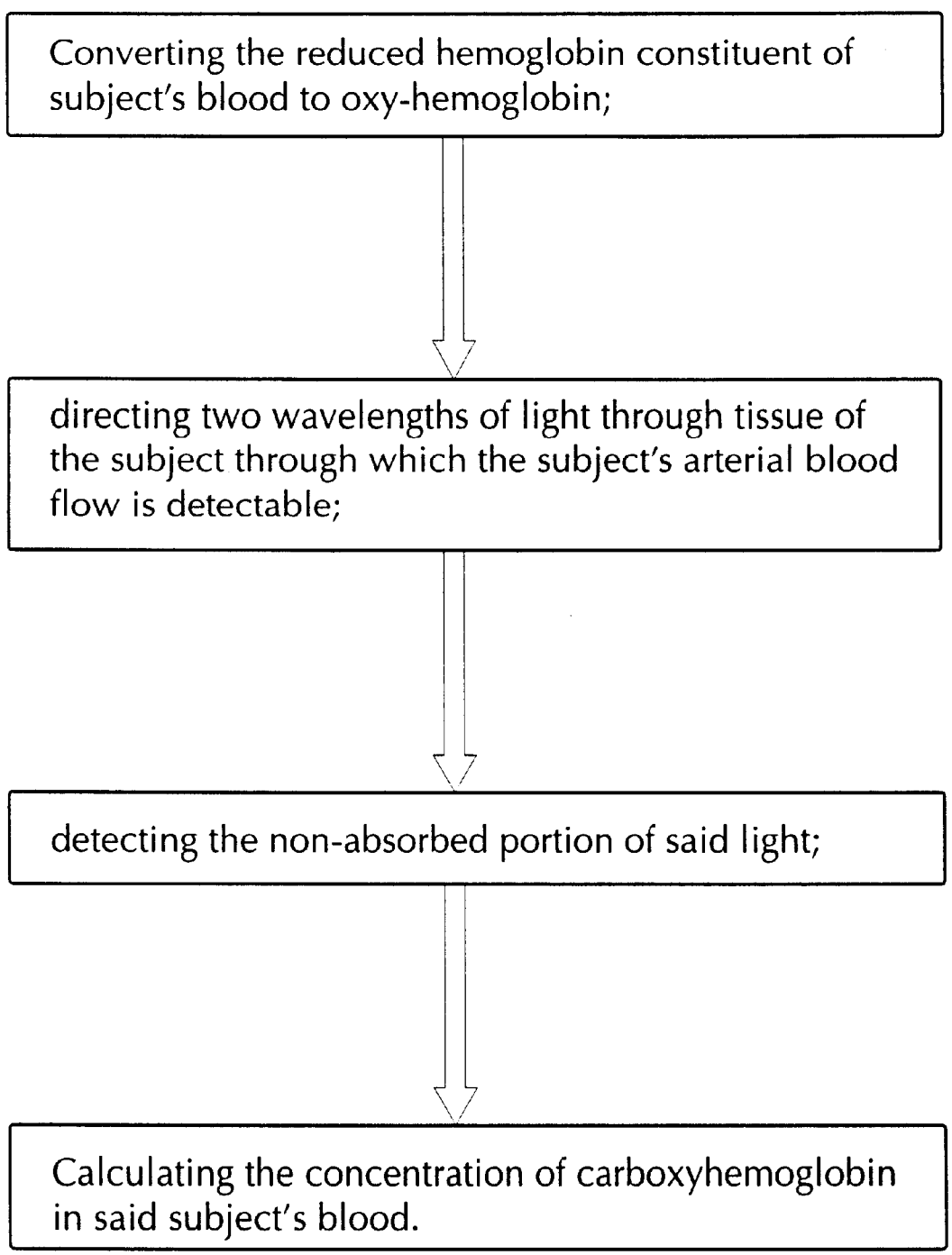
FIG. 2 is a flow chart delineating the steps of the method claimed for measuring carboxyhemoglobin concentrations in a subject's blood.

As shown in more detail in FIG. 5, the two LEDs 202 and 204 are controlled by a microprocessor 210, which monitors the light detector 220 output and adjusts power to the LEDs 202 and 204 to maintain light detector output within an optimal range. The output of the light detector 220 is amplified and filtered and, controlled by the microprocessor, separated into two channels, red and infrared, depending upon which LED is illuminated at any particular time. The DC component of each photoplethysmogram is removed by subtraction from the raw signals, resulting in an AC filtered signal. The AC component of each photoplethysmogram is digitized by a microprocessor-controlled analog-to-digital converter.

The LEDs 202 and 204 are alternatively switched on and off at a rapid rate, e.g., 100–600 HZ, such that only one of the two LEDs is emitting light at any one time. The light that is not absorbed by the tissue and arterial blood of the finger 110 is detected by the light detector 220 on the arm 124 opposite the LEDs 202 and 204. The clamp 102 is designed so as to direct and focus the light emitted by the LEDs 202 and 204 in a narrow beam that impinges on the light detector 220. The light detector 220 is protected and shielded by the arms 122 and 124 of the clamp 102 so as not to receive ambient light.

Turning back to FIG. 1, the hinge 126 allows the finger 110 to be held firmly in place. Lead 134 provides the information to the LEDs from the microprocessor (not shown) which output and intensity are controlled by the microprocessor. A personal computer or some other device for computing can be substituted for the microprocessor as will be readily recognized by those skilled in the art. The same microprocessor 210 controls the light detector 220 and performs the necessary calculations from this information.

The subject undergoing measurement breathes supplemental oxygen at sufficient flow rate or $FiO_2$ to bring the $SaO_2$ (saturated hemoglobin; which can be measured by a conventional pulse oximeter) to 100%. This usually requires oxygen at 1–2 liters per minute by nasal cannula in normal subjects and varying but usually non-toxic amounts of oxygen in subjects with lung disease. When the conventional pulse oximeter reads 100%, indicating that no reduced hemoglobin is present in arterial blood, the two remaining types of hemoglobin, oxy- and carboxy-, are discriminated using two wavelengths.

Figure 3:
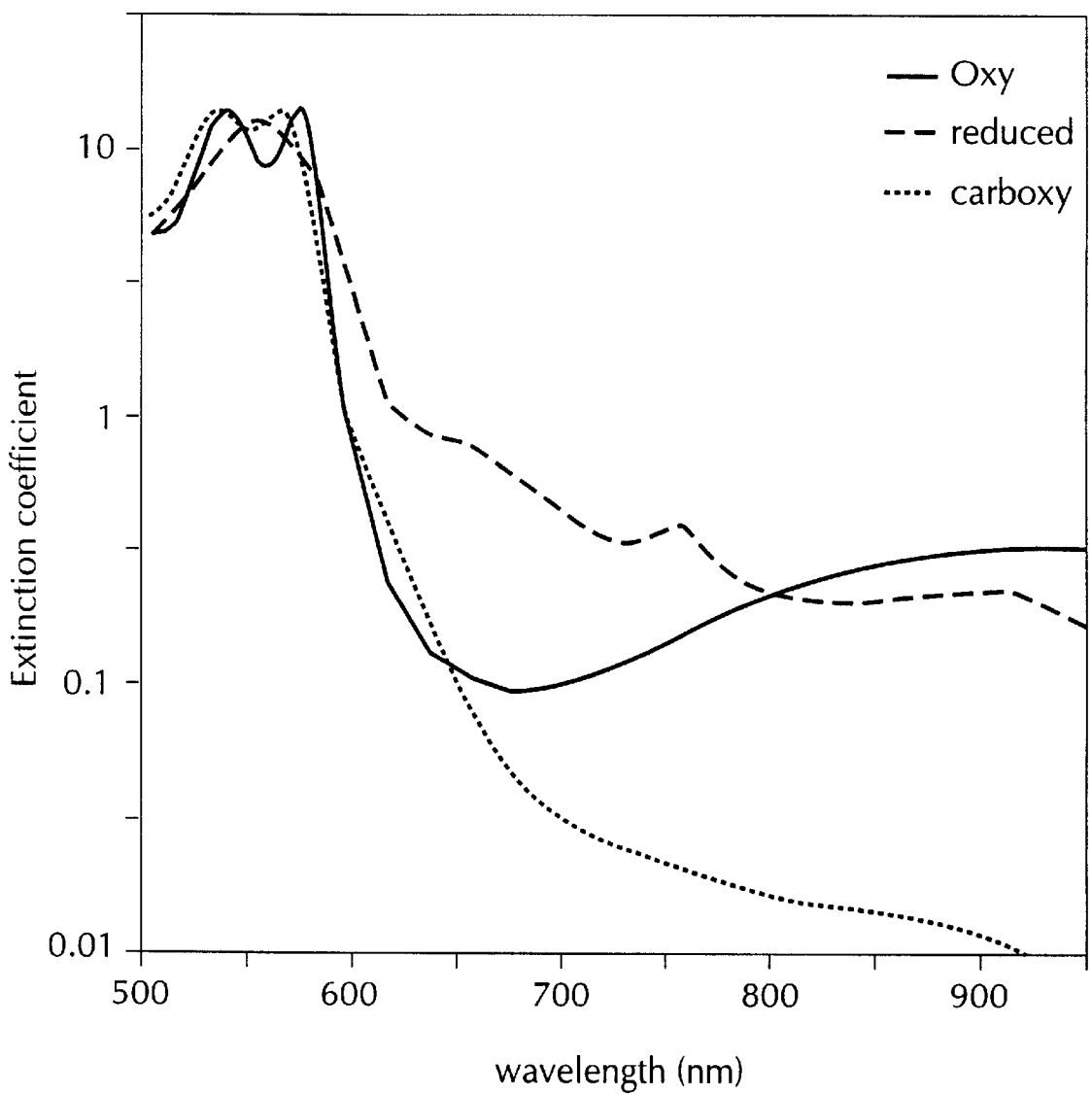
FIG. 3 is a graph illustrating the optical absorbance spectra of oxy-, reduced and carboxyhemoglobin.
Figure 3A:
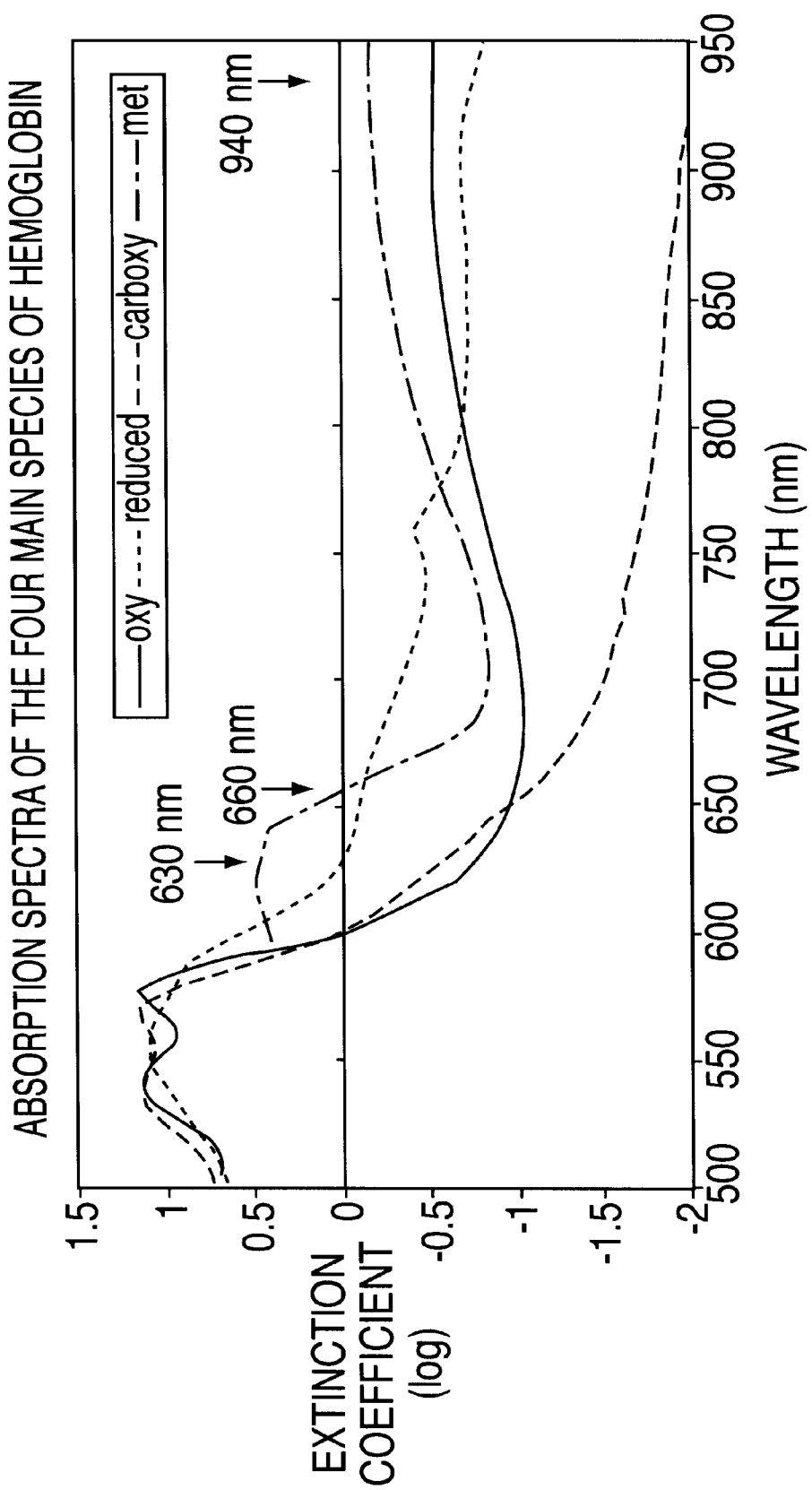
FIG. 3A is a second graph illustrating the same optical absorbance spectra as FIG. 3, but also including the spectra for met-hemoglobin.

As illustrated by FIG. 3, based upon the absorbance spectra of oxy- and carboxyhemoglobins, use of the standard pulse oximeter wavelengths of 660 and 940 nm and increasing the gain on the instrument should allow oxy- and carboxyhemoglobins to be separated, as long as no reduced hemoglobin is present in arterial blood.

Figure 6:
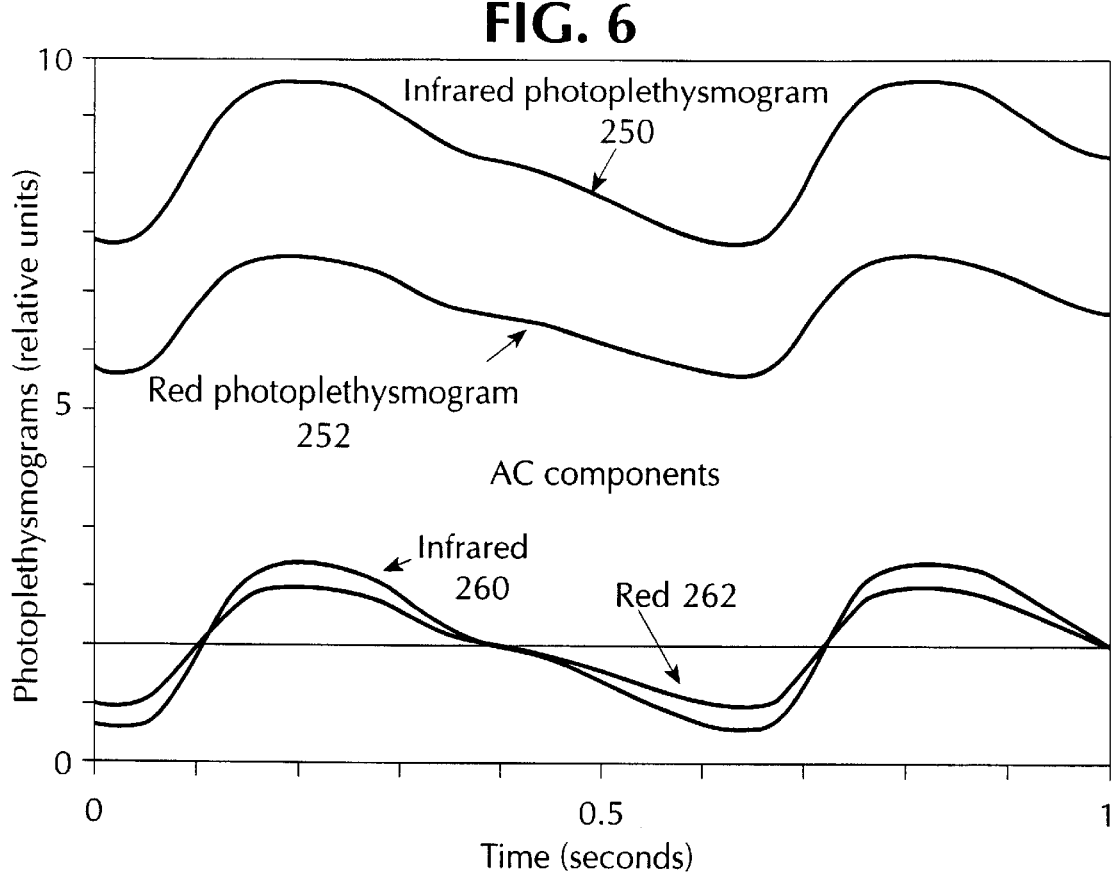
FIG. 6 is a graph of photoplethysmograms from the red and infrared transillumination of the finger.

FIG. 6 is a graph of photoplethysmograms from the red and infrared transillumination of the finger. The top two tracings represent raw photoplethysmograms, the raw infrared (940 nm) photoplethysmogram 250 being the uppermost of the two tracings, and the raw red (660 nm) photoplethysmogram 252 below the infrared tracing 250. The bottom two tracings in the graph represent the AC component of the infrared photoplethysmogram 260 and the AC component of the red photoplethysmogram 262. The AC components are derived by calculating averages for both photoplethysmograms over 60 seconds, then subtracting the average from the raw data.

Figure 7:
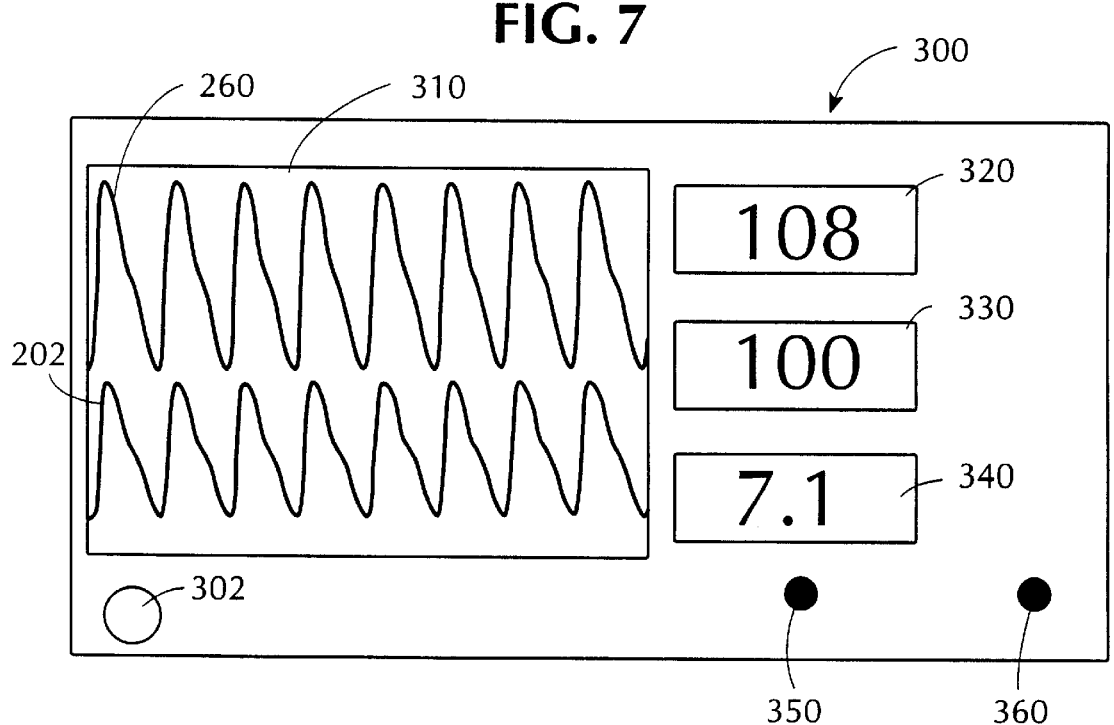
FIG. 7 is a drawing of a preferred embodiment of the display portion of the inventive carboxyhemoglobin monitoring device.

FIG. 7 illustrates a preferred embodiment of the display 300 of the inventive carboxyhemoglobin monitoring device. The display unit 300 illustrated is for the preferred embodiment where the device has two modes, first acting as a pulse oximeter and capable of reading oxygen saturation of hemoglobin. The second mode in the preferred device would be capable of comparing readings to calibration curves for carboxyhemoglobin and switching between the two modes in circumstances described below.

The display unit 300 is preferably attached to the microprocessor 210 and displays the output from the microprocessor 210. Probe 134 (from FIG. 1) plugs into the socket 302. The AC components of the two photoplethysmograms (infrared 260 and red 262) are displayed as a moving display of voltage vs. time in window 310. Heart rate is calculated by the microprocessor by measuring peak to peak time differences in one of the photoplethysmograms and is displayed in window 320. Effective $SaO_2$ (the $SaO_2$ reading that would be obtained from a standard pulse oximeter, for which carboxyhemoglobin is assumed to be zero (possibly erroneously)) is displayed in window 330 and carboxyhemoglobin level is displayed in window 340. The carboxyhemoglobin level display 340 will not be activated until either the effective $SaO_2$ level 330 reads 100% or approaches 100% and does not change over five minutes, during which time the subject has been breathing supplemental oxygen.

Activator 350 activates a timer. The timer is activated when supplemental oxygen is first provided to the subject. The timer tracks the amount of time during which the subject has breathed supplemental oxygen and, as described below, when the time is 5 minutes without a change in $SaO_2$, will switch the mode from a conventional pulse oximeter (reading $SaO_2$) to the inventive monitor of carboxyhemoglobin. The same switch will be made if the $SaO_2$ of the subject reads 100%. Power switch 360 activates the monitoring device.

Figure 4:
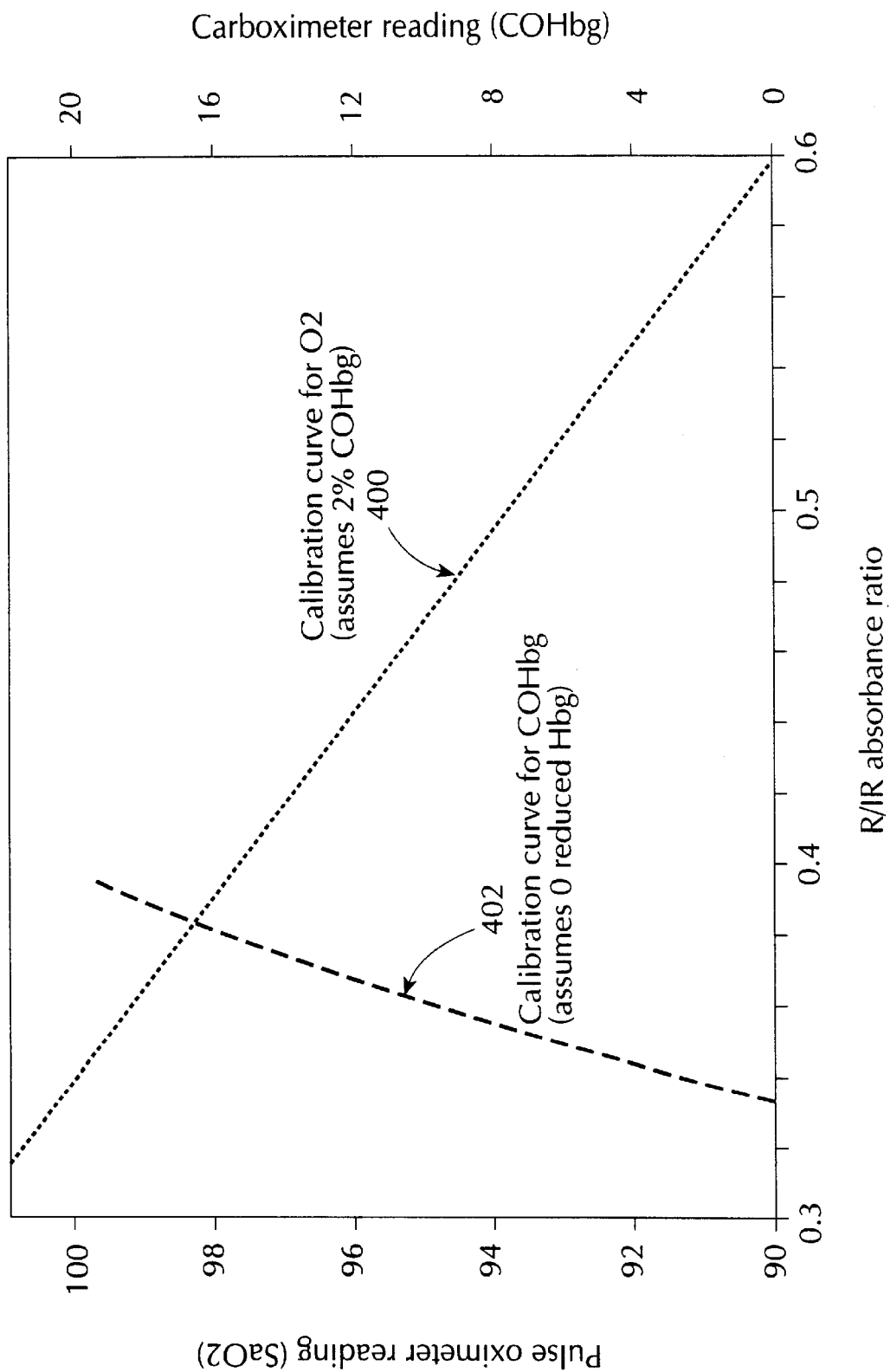
FIG. 4 is a graph illustrating the calculated pulse oximeter readings for various IR/R transmittance ratios (equivalent to R/IR absorbance ratios) on the uppermost (dotted) line and calculated CO-Hgb percentages on the lower (dashed) curve.

FIG. 4 is a graph of hypothetical calculated pulse oximeter readings for various R/IR absorbance ratios 400. This is a hypothetical calibration curve which would be used in the monitoring device when the device is used in the pulse oximeter mode to monitor saturated oxygen levels. Line 402 is a hypothetically calculated CO-Hgb percentage determined by co-oximetry and/or gas-chromatography in nonsmokers, whose carboxy levels range between 0 and 5%, and in cigarette smokers, whose carboxyhemoglobin levels range between 5 and 15%. Calibration beyond 15% is by extrapolation, but could be verified by paired measurements in victims of smoke inhalation.

Line 400 in FIG. 4 shows the relationship between red/infrared absorbance ratio (R/IR) and pulse oximetry reading ($SaO_2$) in normal subjects, whose carboxyhemoglobin levels are low, averaging about 2%. Line 402 shows the relationship between red/infrared absorbance ratio and carboximeter reading (CO-Hgb percentage) in subjects breathing supplemental oxygen. These calibration curves are theoretical, calculated using approximate extinction coefficients for oxy- and carboxyhemoglobin at the two wavelengths. Actual calibration curves would be generated by comparison with CO-oximeter data.

Preferably, the carboxyhemoglobin monitoring device would initially operate as a standard pulse oximeter, reading R/IR and reporting effective oxygen saturation, according to the calibration curve 400 in FIG. 4. When the pulse oximetry reading reaches 100% or approaches 100% and does not increase further with continued oxygen breathing for 5 minutes, the instrument's second channel would switch on, reading R/IR, and reporting carboxyhemoglobin percentage according to the calibration curve 402. While this is the preferred mode, the invention contemplates an instrument that could be operated in a single mode, where R/IR absorbance ratios are calculated and compared to the calibration curve set up for carboxyhemoglobin.

A hypothetical example is shown in FIG. 6. Tracings of red 252 and infrared 250 photoplethysmograms are shown at the top, while the AC components of red 262 and infrared 260 (raw photoplethysmograms minus average [DC] data) are shown at the bottom. Both signals are digitized at a rapid sampling frequency (200–600 Hz) and rate of change is calculated as the difference between sequential data points divided by the time difference. To reduce errors, data points are deleted if the absolute value of the rate of change of either AC signal is less than 10% of the maximal rate of change or if the ratio of the change in infrared signal to change in red signal is less than 0 (indicating that the changes are in opposite directions). The remaining data points are averaged over a 60 second period, and the standard deviation is calculated. Any data point that falls outside two standard deviation of the mean is deleted and the data are again averaged. The resulting mean IR/R transmission ratio (equivalent to R/IR absorbance ratio) is compared to the standard curves found in FIG. 4 (either 400 when the instrument is in the effective $SaO_2$ mode, or 402 when the monitor is reading in the second mode for carboxyhemoglobin) to produce an estimate of effective $SaO_2$ or carboxyhemoglobin percentage, respectively.

In this hypothetical example, using calibration curve 402, if the final average R/IR ratio in the carboxyhemoglobin mode was 0.35, the corresponding carboxyhemoglobin level is about 7%.

In order to avoid problems with the signal-to-noise ratio of the photoplethysmogram caused by the very low absorbance of carboxyhemoglobin in the infrared band, an alternate LED, possibly one emitting in the 560, 565, 620, 630, 700 750 nm range, where carboxy- and oxy-hemoglobins absorb differently, but both are in a middle range of absorbance, may be installed in place of the 940 nm LED.

An alternative apparatus consists of a standard pulse oximeter, with LEDs emitting at 660 and 940 nm transilluminating a fingertip or other body part, and a second modified pulse oximeter, for example illustrated in FIG. 1, with LEDs emitting at 630 and 940 nm transilluminating another fingertip or other body part. Each pulse oximeter sequentially switches on one or the other or neither LED at a rapid rate, approximately 600 Hz. A photodiode responds to incident light allowing transmission of each wavelength of light to be recorded and monitored.

Each arterial pulse is identified as a dip in transmitted light at one of the wavelengths. For each pulse, at each wavelength, the preceding maximum of light transmission (peak diastole) is identified. For each wavelength, all subsequent data until the next minimum of light transmission (peak systole) are expressed as factions of the preceding maximum. For each wavelength, absorbance changes during the pulse are then calculated as the common logarithm of the reciprocal of relative transmission.

For each wavelength during each pulse, the slope of absorbance over time is calculated at mid-systole. For each of the oximeters, a ratio of changing absorbance at the two wavelengths is calculated and averaged over 30 to 60 pulses, yielding two ratios: $\Delta A_{660}/\Delta A_{940}$, and $\Delta A_{630}/\Delta A_{940}$. Carboxyhemoglobin percentage (COHb %) is then calculated from an empirically-determined formula employing two variables, $\Delta A_{660}/\Delta A_{940}$ and $\Delta A_{630}/\Delta A_{940}$. Although the 660 and 630 nm wavelength are collected from two different body parts and so may be measuring pulses of differing volumes, referencing each of them to a second wavelength, in this case 940 nm, corrects for varying pulse volumes.

Figure 8:
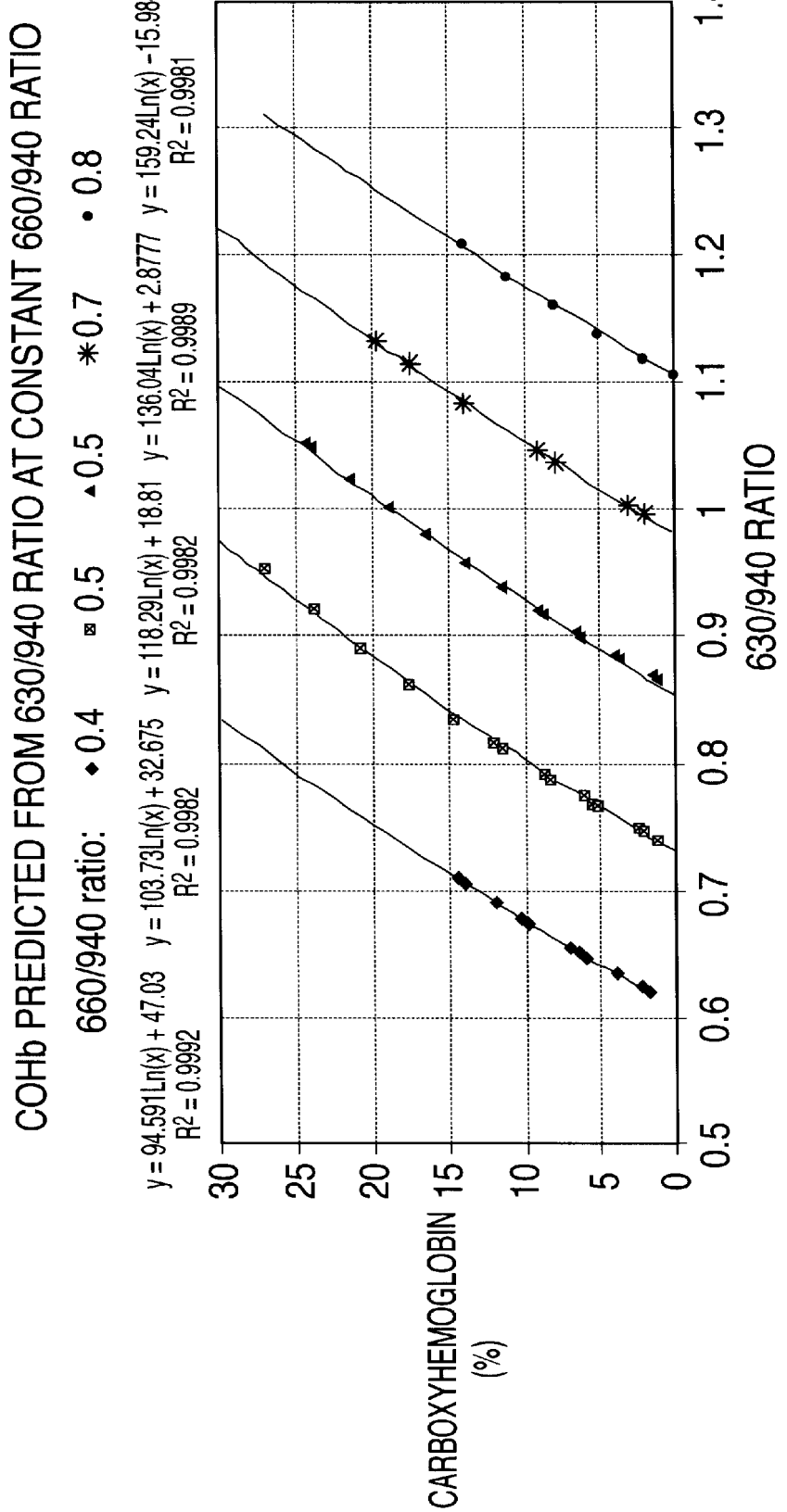
FIG. 8 is a graph depicting the prediction of carboxyhemoglobin levels from the ratio of absorbance changes between one pair of wavelengths (630 and 940 nm) at various levels of the ratio of absorbance changes between another pair of wavelengths (660 and 940 nm).

Using known extinction coefficients for oxy-, reduced, and carboxyhemoglobins, the absorbances at 630, 660 and 940 nm for blood samples with widely varying concentrations of each of the three main species of hemoglobin were calculated. Multiple linear regression analysis demonstrated a highly significant correlation of carboxyhemoglobin against the two ratios, $\Delta A_{660}/\Delta A_{940}$ and $\Delta A_{630}/\Delta A_{940}$, with $R^2=0.9944$, and with the following formula: COHb %=$(127 \cdot \Delta A_{630}/\Delta A_{940})-(159 \cdot \Delta A_{660}/\Delta A_{940})-13$. For data with constant levels of $\Delta A_{660}/\Delta A_{940}$ ratio, carboxyhemoglobin was strongly correlated with $\Delta A_{630}/\Delta A_{940}$ and use of the natural logarithm of $\Delta A_{630}/\Delta A_{940}$ improved the correlations slightly (see FIG. 8). Thus, on a theoretical basis, a combination of the two ratios should provide a highly accurate estimate of carboxyhemoglobin percentage.

It will be recognized that LEDs do not emit strictly monochromatic light; their emissions comprise a band of wavelengths centered around their peak. For that reason, actual data correlating measured carboxyhemoglobin with measured $\Delta A_{660}/\Delta A_{940}$ and $\Delta A_{630}/\Delta A_{940}$ may not follow these theoretical curves and may not correlate as well as the theoretical data. Nevertheless, the addition of a second ratio of changing absorbances should allow accurate enough measurements of carboxyhemoglobin to serve as a reliable screen for carbon monoxide poisoning.

The instrument would be calibrated by empiric comparisons of measured $\Delta A_{660}/\Delta A_{940}$ and $\Delta A_{630}/\Delta A_{940}$ ratios with measured carboxyhemoglobin in arterial blood from heavy smokers breathing (for a few minutes at a time) a range of oxygen concentrations to yield arterial oxygen saturations of 80–100% and studied over a period of several hours of abstinence from smoking, during which carboxyhemoglobin will fall from approximately 5% to approximately 0. Victims of carbon monoxide poisoning will also be studied over a period of several hours as they are being treated with hyperbaric oxygen.

It will be recognized that rather than the $\Delta A_{660}/\Delta A_{940}$ ratio, $S_pO_2$ (measured oxygen saturation, using standard pulse oximetry) could be used as one of the two parameters used to calculate carboxyhemoglobin. For patients being treated for CO poisoning, using hyperbaric oxygen therapy, $S_pO_2$ will be 100%, and COHb % will be a simple linear function of the common logarithm of $\Delta A_{630}/\Delta A_{940}$.

The ideal configuration of an instrument to measure carboxyhemoglobin would be to combine the two pulse oximeters in one cabinet and to display carboxyhemoglobin along with oxyhemoglobin percentage (calculated either as the standard $S_pO_2$ measurement minus the carboxyhemoglobin measurement, or from both the $\Delta A_{660}/\Delta A_{940}$ and the $\Delta A_{630}/\Delta A_{940}$ ratios, using multiple regression data of oxyhemoglobin against the two ratios); essentially, two measurements, the $\Delta A_{660}/\Delta A_{940}$ and $\Delta A_{630}/\Delta A_{940}$ ratios, are used to measure two unknowns, the reduced to total hemoglobin ratio and the carboxy- to total hemoglobin ratio. Carboxyhemoglobin is then expressed as a percentage and oxyhemoglobin is calculated as 100% minus carboxyhemoglobin minus reduced hemoglobin.

Figure 9:
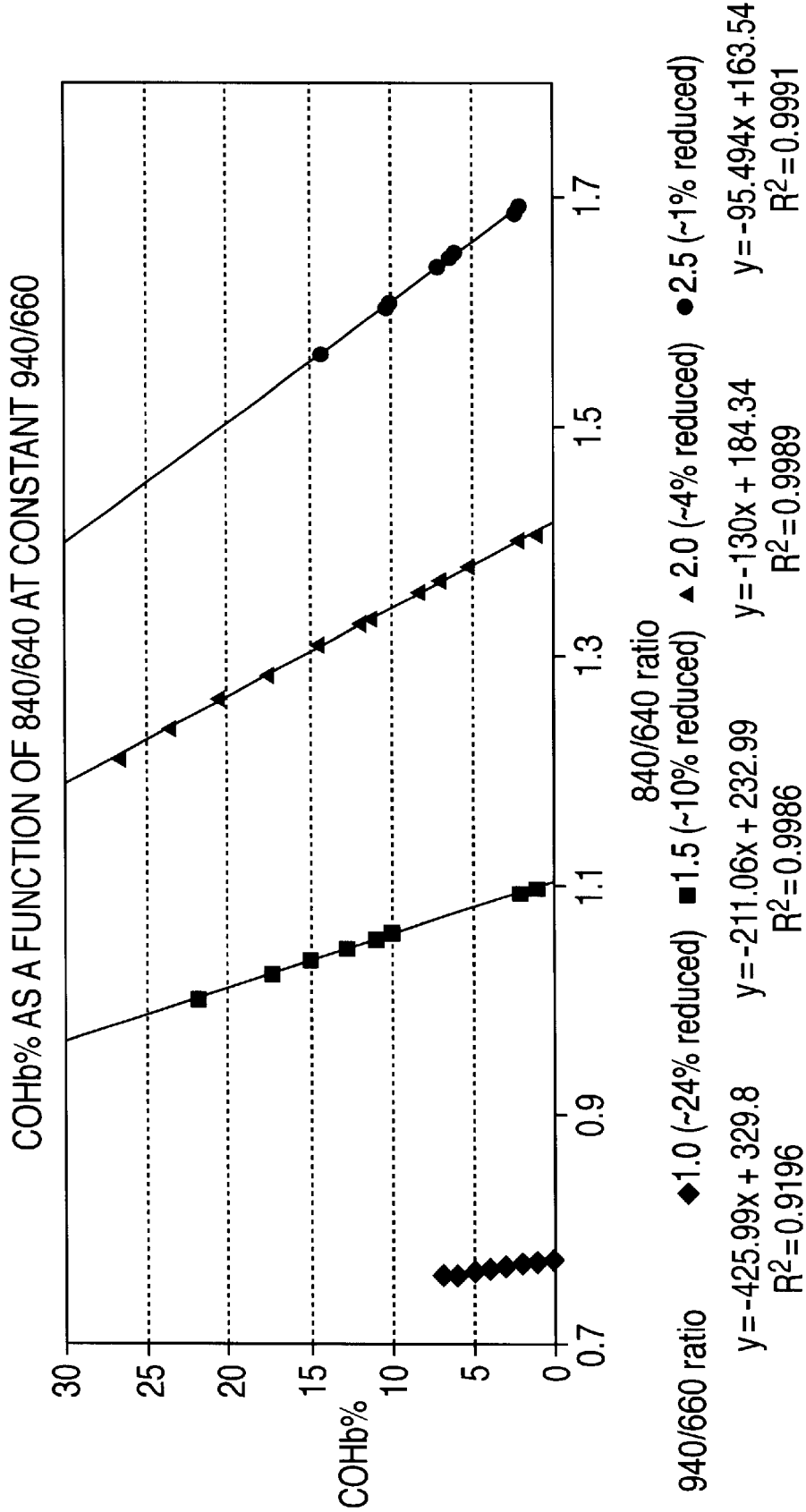
FIG. 9 is a graph depicting the prediction of carboxyhemoglobin levels from the ratios changing absorbance between one pair of wavelengths (840 and 640 nm) at various levels of the ratio of absorbance changes between another pair of wavelengths (940 and 660 nm).

It will be recognized that many other possible wavelength combinations could be used. One alternate would be to use a standard pulse oximeter, with its standard 660 and 940 nm wavelengths, on one finger and a pulse volume photoplethysmograph of the type used in vascular laboratories, with its combination of 640 and 840 nm wavelengths, on another body part. Calculations from theoretical data demonstrate highly significant linear relationships between COHb % and 840/640 absorbance ratios at constant levels of 940/660 ratio (see FIG. 9). The slope is steepest, and therefore resolution best, at high 940/660 ratio, corresponding to low percentage of reduced hemoglobin. At very high levels of reduced hemoglobin (approximately 24%), accuracy of the carboxyhemoglobin measurement would be poor, but, under such circumstances, the standard pulse oximeter would read well below 80%, which would prompt further investigation and intervention, including oxygen administration, which, in itself, would improve the accuracy of subsequent carboxyhemoglobin measurements.

A further refinement would be to add a third oximeter and a third ratio of wavelengths, possibly approximately 700 nm referenced to 940 nm, to allow met-hemoglobin to be detected and quantified by multiple regression against three variables: the 660/940 ratio, the 630/940 ratio, and the 700/940 ratio. Alternatively, since met-hemoglobinemia is characterized by the inability of oxygen administration to bring the standard pulse oximeter reading to 99–100%, whereas carboxyhemoglobinemia is characterized by a spuriously high standard pulse oximeter reading, measurements of changing 660/940 and 630/940 absorbance ratios could be taken, both while the subject breathes room air and after administration of supplemental oxygen. If supplemental oxygen fails to bring the standard pulse oximeter reading to near 100%, then he instrument would assume virtually absent carboxyhemoglobin and read met-hemoglobin from a set of calibration data that assumes the absence of carboxyhemoglobin, whereas, if supplemental oxygen administration results in 99–100% readings from the standard pulse oximeter, the instrument would assume virtually absent met-hemoglobin and read carboxy-hemoglobin from a set of calibration data that assumes the absence of met-hemoglobin. In either case, it would be understood that the carboxy- and met-hemoglobin readings would be estimates only, used primarily to exclude significant carboxyhemoglobinemia or methemoglobinemia or to follow the progress of therapy for either condition.

Although an exemplary embodiment of the invention has been described in detail above, those skilled in the art will readily appreciate that many additional modifications are possible in the exemplary embodiment without materially departing from the novel teachings and advantages of the invention. Accordingly, all such modifications are intended to be included within the scope of the invention as defined in the following claims.

What is claimed is:

1. A non-invasive method for measuring the relative concentration or percentage of carboxyhemoglobin in a subject's blood, said method comprising the steps of:
   a. directing light at a first pair of two different wavelengths through tissue of the subject in which pulsatile flow of blood through an arterial blood vessel can be detected;
   b. directing light at a second pair of two different wavelengths through tissue of the subject in which pulsatile flow of blood through an arterial blood vessel can be detected, at least one of the wavelengths of the second pair differing from the wavelengths of the first pair;

c. simultaneously determining the pulsatile changes in absorbance of the first and second pairs of wavelengths of light by the subject's arterial blood;

d. determining the ratio of change in absorbance of each of the first and second pairs of wavelengths, and;

e. calculating the concentration of carboxyhemoglobin in said subject's blood by comparing the results of a formula employing the ratios determined in step d as independent variables to the results of the same formula in subjects with known carboxyhemoglobin levels.

2. The method of claim 1, wherein the first pair of wavelengths is approximately 630 and 730 nm and the second pair of wavelengths is approximately 660 and 940 nm.

3. The method of claim 1, wherein the first pair of wavelengths is approximately 940 and 660 nm and the second pair of wavelengths is approximately 940 and 630 nm.

4. The method of claim 1, wherein the first pair of wavelengths is approximately 940 and 660 nm and the second pair of wavelengths is approximately 840 and 640 nm.

5. The method of claim 1, wherein the tissue transilluminated in step b is remotely located from the tissue transilluminated in step a.

6. A non-invasive method for measuring the concentrations of carboxyhemoglobin and met-hemoglobin in a subject's blood, said method comprising the steps of:

a. directing light at a first pair of two different wavelengths through tissue of the subject in which pulsatile flow of blood through an arterial blood vessel can be detected;

b. directing light at a second pair of two different wavelengths through tissue of the subject in which pulsatile flow of blood through an arterial blood vessel can be detected, at least one of the wavelengths of the second pair differing from the wavelengths of the first pair;

c. directing light at a third pair of two different wavelengths through tissue of the subject in which pulsatile flow of blood through an arterial blood vessel can be detected, at least one of the wavelengths of the third pair differing from the wavelengths of the first and second pairs;

d. simultaneously determining the pulsatile changes in absorbance of the first, second and third pairs of wavelengths of light by the subject's arterial blood;

e. determining the ratio of change in absorbance of each of the first, second and third pairs of wavelengths, and;

f. calculating the concentrations of carboxy-hemoglobin and met-hemoglobin in said subject's blood by comparing the results of a formula employing the ratios determined in step e as independent variables to the same ratios determined in subjects with known carboxyhemoglobin and met-hemoglobin levels.

7. The method of claim 6, wherein the third pair of wavelengths is approximately 730 and 940 nm.

8. The method of claim 6, wherein the tissue transilluminated in steps a, b and c are remotely located from one another.

9. A non-invasive method for measuring the concentration of oxy-hemoglobin while accounting for the relative concentration of met-hemoglobin and/or carboxyhemoglobin in a subject's blood, said method comprising the steps of:

a. directing light at a first pair of two different wavelengths through tissue of the subject in which pulsatile flow of blood through an arterial blood vessel can be detected;

b. directing light at a second pair of two different wavelengths through tissue of the subject in which pulsatile flow of blood through an arterial blood vessel can be detected, at least one of the wavelengths of the second pair differing from the wavelengths of the first pair;

c. directing light at a third pair of two different wavelengths through tissue of the subject in which pulsatile flow of blood through an arterial blood vessel can be detected, at least one of the wavelengths of the third pair differing from the wavelengths of the first and second pairs;

d. simultaneously determining the pulsatile changes in absorbance of the first, second and third pairs of wavelengths of light by the subject's arterial blood;

e. determining the ratio of change in absorbance of each of the first, second and third pairs of wavelengths, and;

f. calculating the relative concentrations of oxy-hemoglobin and carboxyhemoglobin and/or met-hemoglobin in said subject's blood by comparing the results of a formula employing the ratios determined in step e as independent variables to the results of the same formula in subjects with known oxy-hemoglobin, carboxyhemoglobin, and met-hemoglobin levels.

* * * * *